United States Patent [19]

Menon et al.

[11] Patent Number: 5,643,554
[45] Date of Patent: Jul. 1, 1997

[54] LIPOMELANIM COMPOSITION

[75] Inventors: I. Avavindakshan Menon, North York; Herbert F. Haberman, Toronto, both of Canada

[73] Assignee: DUSA Pharmaceuticals, Inc., Ontario, Canada

[21] Appl. No.: 54,271

[22] Filed: Apr. 30, 1993

[51] Int. Cl.$^6$ .............................. A61K 7/42; A61K 31/20
[52] U.S. Cl. .............................. 424/59; 514/553; 514/558; 554/80
[58] Field of Search ................... 554/80; 424/59; 514/553, 558

[56] References Cited

U.S. PATENT DOCUMENTS

| | | | |
|---|---|---|---|
| 3,019,165 | 1/1962 | Mansor | 167/65 |
| 3,506,758 | 4/1970 | Epstein et al. | 424/60 |
| 4,021,538 | 5/1977 | Yu et al. | 424/60 |
| 4,256,664 | 3/1981 | Epstein et al. | 564/177 |
| 4,390,341 | 6/1983 | Jacobs | 8/424 |
| 4,434,154 | 2/1984 | McShane | 424/60 |
| 4,453,941 | 6/1984 | Jacobs | 8/424 |
| 4,454,112 | 6/1984 | Tuominen | 424/60 |
| 4,508,706 | 4/1985 | Pawelek et al. | 424/60 |
| 4,515,773 | 5/1985 | Herlihy | 424/59 |
| 4,537,782 | 8/1985 | Millet et al. | 514/774 |
| 4,609,544 | 9/1986 | Herlihy | 424/59 |
| 4,714,609 | 12/1987 | Carden | 424/59 |
| 4,776,857 | 10/1988 | Carroll et al. | 8/423 |
| 4,783,332 | 11/1988 | Schreuder | 424/59 |
| 4,806,344 | 2/1989 | Gaskin | 424/59 |
| 4,956,174 | 9/1990 | Lang et al. | 424/63 |
| 4,968,497 | 11/1990 | Wolfram et al. | 424/59 |
| 5,037,640 | 8/1991 | Schultz et al. | 424/59 |
| 5,061,480 | 10/1991 | Marchese et al. | 424/59 |
| 5,075,113 | 12/1991 | DuBois | 424/450 |
| 5,080,889 | 1/1992 | Katada et al. | 424/63 |
| 5,157,075 | 10/1992 | Kanai et al. | 525/54.1 |
| 5,210,076 | 5/1993 | Berliner | 514/21 |
| 5,256,403 | 10/1993 | Gaskin | 424/59 |

FOREIGN PATENT DOCUMENTS

WO90/10430  9/1990  WIPO.
WO94/00097  1/1994  WIPO.

OTHER PUBLICATIONS

"Factors Affecting the Reliability of Sunscreen Protection Factors", B.L Diffey, pp. 111–118.

"Eumelanins and Pheomelanins: Characterization by Electron Spin Resonance Spectroscopy", Roger Sealy, et al., Science, vol. 217, pp. 545–547 (1982).

"Some New Aspects of Eumelanin Chemistry", G. Prota, Advances in Pigment Cell Research, pp. 101–124 (1988).

"Novel free radicals in synthetic and natural pheomelanins: Distinction between dopa melanins and cysteinyldopa melanins by ESR spectroscopy".

Roger Sealy, et al., Proc. Natl. Acad. Sci. USA, vol. 79, pp. 2885–2889 (1982).

"Role of Reactive Oxygen Species and Free Radicals from Melanins in Photo–induced Cutaneous Inflammations", Pathol. Immunopathol. Res., vol. 5, pp. 118–139 (1986).

(List continued on next page.)

*Primary Examiner*—Shelley A. Dodson
*Attorney, Agent, or Firm*—Medlen & Carroll, LLP

[57] ABSTRACT

A novel lipomelanin sunscreen complex includes melanin linked to a lipid to form a lipomelanin. One or more ultra-violet-light absorbing compounds can be added to form a lipomelanin sunscreen complex. A method for making the complex includes the oxidization of DOPA in the presence of a lipid and one or more ultra-violet absorbing compounds to form a mixture and precipitating the complex from the mixture by the addition of acid. The lipomelanin sunscreen complex provides protection against harmful ultra-violet radiation. The level of UV protection may be varied according to the presence and properties of the ultra-violet absorbing compounds in the complex.

26 Claims, 8 Drawing Sheets

OTHER PUBLICATIONS

"A Comparative Study of the Physical and Chemical Properties of Melanins Isolated from Human Black and Red Hair", I. Aravindakshan Menon, The Journal of Investigative Dermatology, vol. 80, No. 3 (1983), pp. 202–206.

"Mass–Producing Nature's Sunscreen", Gene Bylinsky, Fortune, p. 131 (1992).

Fragrance J vol. 18, No. 6, pp. 86–93 (1990) (FIG. 17, Ref. 19) Ando et al (Abstract).

Chem. Abs., vol. 117 (26): 257988d, Pauelek et al.

Chem Abs. vol. 116(8):66915q, Junino et al.

◇ Lipid melanin with ASA (with tyrosinase)
● Lipomelanin with ASA (without tyrosinase)
□ Lipomelanin with ASA (without tyrosinase) plus PABA
▽ Lipomelanin with ASA (without tyrosinase) plus benzophenone

FIG. 8.

LIPOMELANIN COMPOSITION

FIELD OF THE INVENTION

The present invention relates to novel sunscreen complexes. In particular, the present invention relates to ultra-violet-light absorbing compositions containing Melanin.

BACKGROUND OF THE INVENTION

Melanins are the major pigments of hair, skin and eyes. Naturally occurring melanins can be of a variety of colours, such as black, brown and red. Two major categories of melanins are known; eumelanins which provide a black or brown pigmentation, and pheomelanins, which provide a yellow to reddish-brown pigmentation. Natural suntanning occurs through exposure of the skin to light radiation at a wavelength of 280–400 nm.

For most individuals the sensitivity of the skin to ultra-violet radiation (hereinafter referred to as "UVR") is largely determined by its melanin content. The amounts and types of melanin present in the skin vary from person to person and, thus, the tolerance of the skin when exposed to UVR varies from person to person. For most individuals the greater the melanin content of the skin of an individual, the more tolerant is the skin of that individual to UVR.

Melanins are complex heteropolymers, of which the biosynthetic pathways and exact chemical structure are unknown. However, melanins are believed to be copolymers of 3,4-dihydroxyphenylalanine (DOPA) and cysteinyldopa. While the inventors do not intend to be limited to any particular scheme of synthesis, it is believed that the in vivo synthetic pathway leading to the production of melanin begins with the enzymatic oxidation of the amino acid, tyrosine, to form DOPA, and continues in the presence of the enzyme tyrosinase (polyphenol oxidase) with a series of oxidation and polymerization reactions to result in melanin. This postulated synthetic pathway may be represented as follows:

-continued dopachrome 5,6-dihydroxyindole indole-5-6-quinone

↓ eumelanins

5-S-cysteinyldopa

↓ benzothiazine

↓ pheomelanins

Melanins may also be produced by the auto-oxidation of DOPA, whereby the production of melanin occurs in the absence of tyrosinase.

Thus, it is believed that known melanins, or compounds with the same or similar functional features as known melanins, may be produced either naturally or synthetically from DOPA, analogs of DOPA or biosynthetic precursors of DOPA. As used herein, "melanins" includes all such known melanins or melanin products, however derived, and all melanin-like compounds or analogs with the herein-described pigment and photoprotective functions.

The photoprotective function of melanin is believed to be associated with both its physical and biochemical properties. Melanin is believed to dissipate UVR into heat which is absorbed, and to promote oxidation reactions and quench free radicals, the formation of which is induced by UVR. Melanin is able to function as a stable free radical, thus resulting in its ability to quench damaging free radicals formed in the skin on exposure to UVR. The role of melanin as a free radical scavenger is significant in its photoprotective role in individuals having a moderate or greater melanin content in their skin; however, it is highly desirable that individuals having a minimal melanin content in their skin supplement the body's natural protective mechanism to UVR with a topical sunscreen supplement. It is now recognized that even individuals with moderate or greater levels of melanin should supplement this natural protective mechanism when longer exposure to UVR is anticipated.

As a result of the increasing awareness of the public of the detrimental effects of exposure to UVR, a variety of sunscreen compositions for topical administration have been developed. Various salicylate compounds have been described as sunscreen agents due to their ability to absorb UVR. For example, U.S. Pat. Nos. 3,506,758 and 4,256,664 describe compositions for use as sunscreens which include the esterification product of p-aminobenzoic acid (paba) and/or salicylic acid with lecithins, choline and/or imidazoles having a reactive hydroxyl group. U.S. Pat. No. 4,454,112 describes tocopherol acetylsalicylate compounds which are useful as sunscreen agents in compositions for topical administration. However, it has been found that salicylate compounds may cause skin irritations and allergic reactions in some individuals, and, as a result, are not ideal as the primary components of such topical compositions.

A common UVR absorbing compound found in sunscreen compositions is paba, and esters of paba, such as octyl dimethyl paba [octyl-p-(dimethyl-amino) benzoate]. U.S. Pat. No. 4,434,154 teaches one such UVR protective composition which contains an emulsion of octyl dimethyl paba, dihydroxy acetone, water, oil and a surfactant.

Sun protectant compositions have also been described which contain melanin. However, the known methods of making melanin have disadvantages. With both the enzymatic and auto-oxidation methods for preparing melanins, the properties of the melanin product obtained make it undesirable for incorporation into a sunscreen composition for application onto the skin. Specifically, the melanins obtained are granular in nature, which results in a product that cannot be spread evenly when applied to the skin. These melanins are also undesirable in that they are not easily absorbed by the skin under acceptable physiological skin conditions (i.e. neutral pH). Further, the effectiveness of these melanins is limited with respect to ultra-violet absorption. Specifically, the absorption capacity of the melanins produced by either of these methods is low in the short-wave range (UVB) of the ultra-violet spectrum. U.S. Pat. No. 4,806,344 describes one such melanin composition additionally comprising ferric chloride, triethanolamine, a sunscreen compound such as paba and a cosmetic base in the form of an oil, cream or ointment.

Many of the sunscreen products currently available do not fully protect the skin against the complete wavelength spectrum of UVR. UVR comprises both long-wave UVR (or UVA, having a wavelength of approximately 320–400 nm) and short-wave UVR (or UVB, having a wavelength of approximately 290–320 nm). Of particular concern for a large portion of the population is protection of the skin against the aging process which is accelerated by exposure to UVR. Long-wave UVA is believed to specifically contribute to the aging process.

Most ultra-violet light absorbing compounds useful as sunscreen agents only absorb within a small range of the wavelength of UVR. Thus, in order to maximize the absorption capacity of UVR in a sunscreen composition, the composition may contain not just a single sunscreen compound but several such compounds which are selected to provide broad range UVR protection. However, sunscreen compositions containing a variety of compounds are more apt to cause allergic or photoallergic reactions in individuals. Allergic and photoallergic reactions to existing sunscreen compounds and compositions is a common occurrence and generally results in dermatitis or photodermatitis. Certain individuals also suffer from skin eruptions due to long UVA and visible light, and a very broad wavelength sunscreen would be valuable for these people.

Thus, it would be desirable to provide a sunscreen composition which imparts effective protection against the broad spectrum of UVR, which is compatible for use with human skin tissue.

SUMMARY OF THE INVENTION

It is an object of the present invention to provide novel melanin-containing compounds, and a method for making such compounds.

Accordingly, in one aspect, the present invention provides a lipomelanin composition formed from a melanin chemically bonded to a lipid compound. In another aspect of the present invention, there is provided a lipomelanin sunscreen complex comprising a melanin bonded to a lipid to form a lipomelanin, wherein said lipomelanin incorporates at least one ultra-violet light absorbing compound.

In yet another aspect of the present invention, there is provided a method for making a lipomelanin comprising the steps of enzymatically converting 3,4-dihydroxyphenylalanine or a suitable analog thereof to melanin, in the presence of a lipid, and isolating the resulting lipomelanin.

In a further aspect of the present invention, there is provided a method for making a lipomelanin sunscreen comprising a melanin chemically bonded to a lipid compound to form a lipomelanin wherein said lipomelanin also includes at least one ultra-violet-light absorbing compound, including the steps of enzymatically converting 3,4-dihydroxyphenylalanine or a suitable analog thereof to melanin, in the presence of a lipid and an ultra-violet light absorbing compound, and isolating the resulting composition.

The novel composition of the present invention comprises melanin bonded to a lipid to form a lipomelanin. The structure is not clearly understood, largely due to the lack of information about the synthesis and structure of melanins. As used herein, "lipomelanins" refers to the novel compounds of the present invention, comprising one or more lipids (as hereinafter more fully described) bonded to one or more melanins. As used herein, "lipomelanin sunscreen" comprises a lipomelanin bonded to an ultra-violet-light absorbing compound.

The lipomelanin sunscreen has been found to absorb UVR and particularly short-wave UVB to a greater extent than melanin alone. Moreover, the inclusion of an ultra-violet absorbing compound to the reaction mixture during the formulation of the lipomelanin advantageously provides a sunscreen compound in which the absorption of both UVA and UVB may be varied by selecting and varying the number and properties of ultra-violet absorbing compound or compounds retained within the lipomelanin sunscreen. Thus, a lipomelanin sunscreen having a high level of absorption of both UVA and UVB may be provided by incorporating the appropriate UV-absorbing compounds into the lipomelanin polymer.

The characteristics of the lipomelanin or the lipomelanin sunscreen of the present invention make it suitable for application to the skin. Specifically, it has the consistency of a smooth cream and thus may be easily mixed with other creams for application to the skin. Its consistency also enables it to be spread evenly on the skin (either alone or in combination with other creams and ingredients) for uniform sunscreen protection. It is soluble at physiological pH making it suitable for application to human skin. Furthermore, it is less allergenic than other sunscreen compounds, thereby making it desirable for use by those having sensitive skin.

In addition to the sunscreen and pigmentation functions of the lipomelanin and lipomelanin sunscreen, the compounds of the present invention may be useful for treatment of certain skin disorders such as hemangioma or vitiligo. Abnormal skin pigmentation and sensitivity to ultra-violet light are associated with these and other disorders, and the compounds of the present invention may function to provide additional pigmentation or standardization of existing pigmentation to skin while still maintaining protection from UVR.

Additionally, the sunscreen and pigmentation aspects of the present invention make it suitable for use as a hair dye composition. The lipomelanin composition can be applied to the hair to provide increased pigmentation.

BRIEF DESCRIPTION OF THE DRAWINGS

Embodiments of the present invention will be described by reference to the following figures in which.

DETAILED DESCRIPTION OF THE INVENTION

In accordance with one aspect of the invention, a lipomelanin is disclosed. The lipomelanin is a compound prepared by oxidization of DOPA or a suitable DOPA analog in the presence of an unsaturated lipid (as hereinafter more fully described). The lipomelanin is creamy and smooth, suitable for application to human skin.

In a further aspect of this invention, a lipomelanin sunscreen is provided. The lipomelanin sunscreen comprises melanin substantially covalently bonded to a lipid and one or more ultra-violet-light absorbing compounds. The lipomelanin sunscreen thus provides protection from the harmful aspects of UVR, while additionally adding pigmentation to the skin of the user.

The term "lipid" as used herein is meant to encompass compounds classified as lipids including fats, phosphoglycerides and fatty acids. Lipids are organic compounds chiefly comprising carbon, hydrogen and oxygen, but may also include other elements. Lipids are insoluble in water, but are soluble in various organic solvents. Included within the lipid family are fats, which are esters of glycerol which hydrolyze to form glycerol and fatty acids. Fatty acids are organic acids comprising carbon and hydrogen and including a carboxyl group. Phosphoglycerides are similar to fats in which one fatty acid component has been replaced by a phosphoric acid component, and may additionally contain nitrogen.

Non-limiting examples of lipids for use as the lipid compound in the lipomelanin sunscreen of the present invention include unsaturated fatty acids; triglycerides; diglycerides; monoglycerides; methyl, ethyl, octyl, and higher molecular weight esters of fatty acids; lecithins (for example phosphatidyl choline); cephalins (for example, phosphatidyl ethanolamine); phosphatidyl dimethylethanolamine; phosphatidyl monomethylethanolamine; phosphatidyl inositol, phosphatidyl serine and phosphatidic acid. Preferably, the lipids of the present invention should be unsaturated (to provide covalent bonding sites), of high molecular weight, with an approximate lower limit of a $C_{10}$ chain length. Preferred fatty acids include but are not limited to long-chain fatty acids such as arachidonic acid, oleic acid, linoleic acid and linolenic acid. Preferred phosphoglycerides for use as the lipid compound in the lipomelanin sunscreen include lecithins.

The lipomelanin sunscreen may incorporate more than one ultra-violet-light absorbing compound. In this way, the effectiveness of the lipomelanin sunscreen may be maximized by incorporating within the lipomelanin polymer compounds which absorb in different wavelengths of the ultra-violet spectrum, for example, in both the short-wave UVB and in the long-wave UVA regions of the UVR spectrum.

The ultra-violet-light absorbing compound may be any compound which absorbs ultra-violet radiation and is suitable for application onto the skin. The United States FDA has disseminated a list of sunscreen and sunblocking agents considered safe and effective for both UVA and UVB. Non-limiting examples of such suitable ultra-violet absorbing compounds for incorporation into the lipomelanin sunscreen include paba, butyl paba, cinoxate, diethanolamine p-methoxycinnamate, digalloyl trioleate, dioxybenzone, amyl dimethyl paba, homomenthyl salicylate, ethyl 4-aminobenzoate, ethyl 4-[bis(hydroxypropyl)] aminobenzoate, 2-Ethyl-hexyl 2-cyano-3,3-dephenylacrylate, ethyl-hexyl p-methoxycinnamate, 2-Ethyl-hexyl salicylate, glycerol aminobenzoate, homosalate, lawsone with dihydroxyacetone, menthyl anthranilate, Padimate A, Padimate 0, 2-Phenylbenzimidazole 5-sulfonic acid, red petrolatum, acetylsalicylic acid, triethanolamine salicylate, octyl dimethyl paba, glycerol paba, 2-hydroxy-4-methoxy-5-sulfobenzophenone (trihydrate) (Sulisobenzone), butyl methoxy benzoylmethane (Parsol 1789), 4-tert-butyl-4'-methoxy-dibenzoylmethane, 2-hydroxy-4-methoxybenzophenone (oxybenzone), isoamyl dimethyl paba ester, 4-hydroxycinnamic acid, benzophenone, and polymers or combinations thereof.

Non-limiting examples of compounds appropriate for incorporation into a lipomelanin sunscreen and known to specifically absorb UVA include oxybenzone, sulisobenzone, dioxybenzone, menthyl anthranilate and Non-limiting examples of compounds appropriate for incorporation into a lipomelanin sunscreen and known to absorb UVB include paba, amyl dimethyl paba, glyceryl paba, octyl dimethyl paba, anthranilates, 2-ethoxyethyl p-methoxycinnamate, diethanolamine p-methoxycinnamate, digalloyl trioleate, ethyl 4-bis-(hydroxypropyl) aminobenzoate, 2-Ethyl-hexyl salicylate, glycerol aminobenzoate, homomenthyl salicylate, lawsone with dihydroxyacetone, 2-Phenyl benzimidazole 5-sulfonic acid and triethanolamine salicylate.

The method for making a melanin sunscreen of the present invention includes oxidizing 3,4-dihydroxyphenylalanine (DOPA) to form melanin. Analogs of DOPA may also be used in accordance with the present invention. Suitable analog compounds may include synthetic analogs or naturally occurring analogs. Non-limiting examples of DOPA analogs include hydroquinone, cathechol, o-quinone, p-quinone, DOPA methyl ester, dihydroxyphenylacetic acid, dihydroxyphenyl glycol and dihydroxyphenyl serine.

DOPA or an analog thereof may be oxidized by aeration. Thus, for example, air is bubbled through a solution of DOPA in an alkaline medium. The solution may also be aerated by rotary movement or shaking. The pH of the alkaline medium may be in the range of from about 7 to about 10. Preferably, the alkaline medium has a pH of about 8. Non-limiting examples of a suitable alkaline medium include sodium phosphate, potassium phosphate, sodium borate, and tris-hydroxy methyl-HCl. Most preferably, the alkaline medium is sodium phosphate buffer at pH 8.0.

The lipid compound, either alone or in conjunction with one or more ultra-violet absorbing compounds is added to the DOPA solution and aeration on a rotary shaker is continued for a time sufficient to oxidize DOPA to form lipomelanin, at least overnight.

In another aspect of the present invention, the melanin may be enzymatically oxidized by tyrosinase. Tyrosinase oxidation occurs at an approximate pH of 6.8, at temperatures of between 20° C. and 37° C.

Upon completion of the oxidation, the resulting lipomelanin is precipitated by addition of inorganic acid to the solution. The acid is not particularly restricted and may include any acid capable of reducing the pH of the final suspension to a pH sufficient for precipitation of the complex, typically below 4, such as hydrochloric acid or sulphuric acid.

The precipitated lipomelanin is removed from the solution by any method suitable for separating solids from liquids. Centrifugation as well as filtration are methods suitable to separate the lipomelanin from the acid medium. In order to purify the lipomelanin, the sediment may be redissolved in a suitable alkaline medium, as set out in the foregoing, and precipitated therefrom by the addition of acid. These purification steps are preferably repeated at least twice in order to remove impurities from the lipomelanin.

Figure 1:
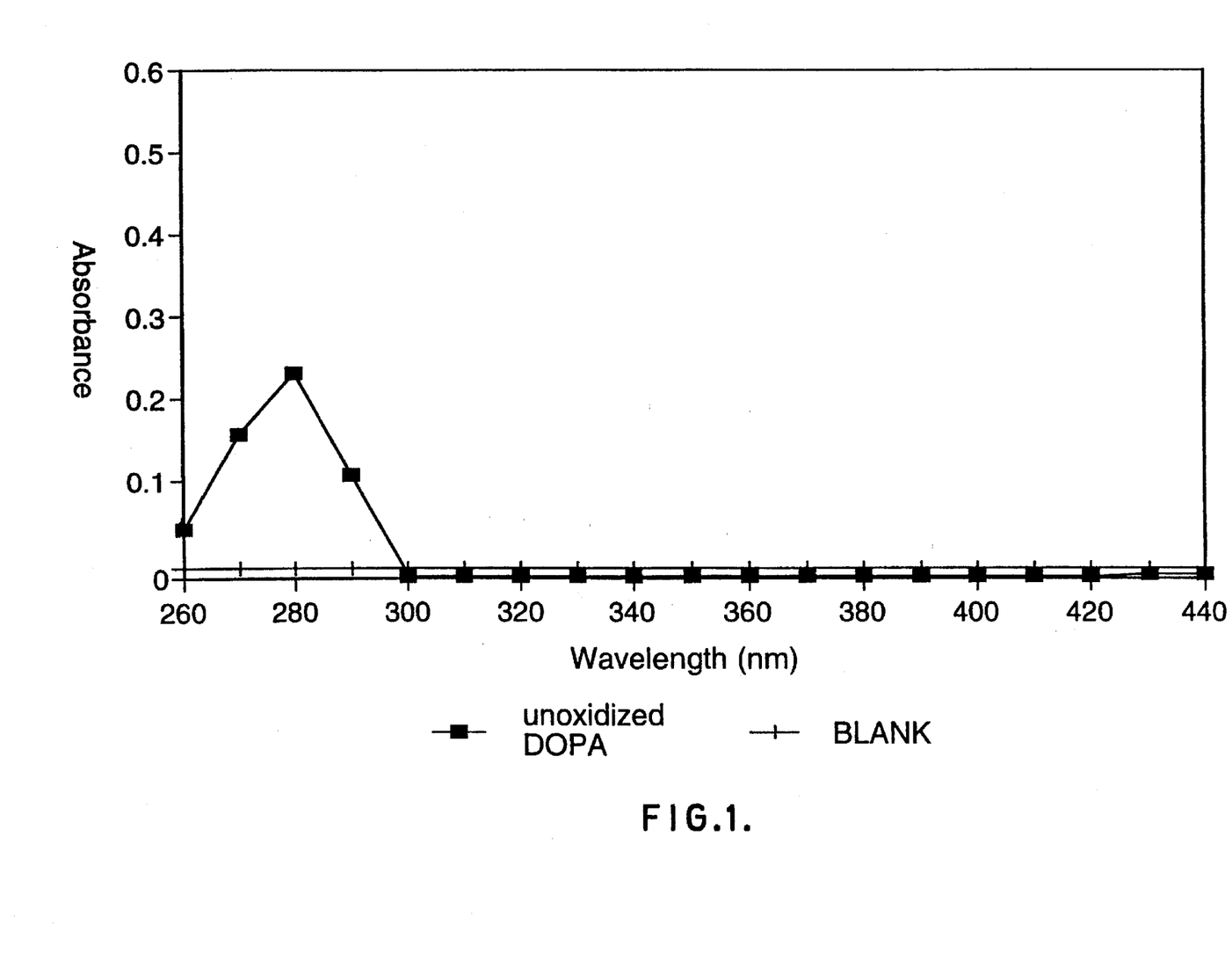
FIG. 1 shows the absorption spectra of unoxidized DOPA, at the wavelengths of from 260 to 440 nm.

The absorption spectra of the novel compounds prepared according to the method of the present invention are noted in the Figures. By way of reference, FIG. 1 shows the absorption spectra, at wavelengths of from 260 to 440 nm, of unoxidized DOPA, together with a blank.

Figure 2:
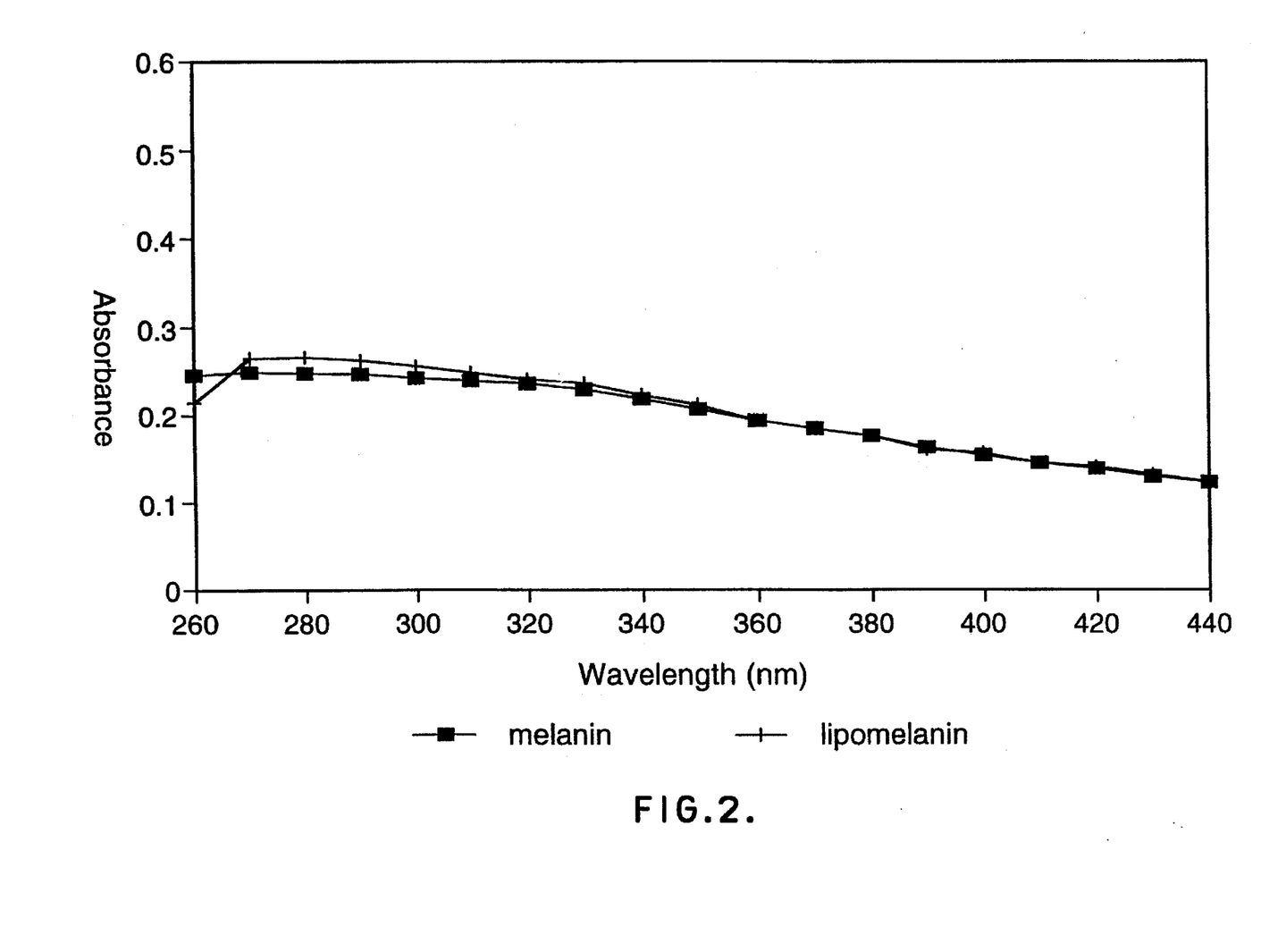
FIG. 2 shows the absorption spectra of melanin and lipomelanin.

FIG. 2 presents the absorption spectra of melanin (oxidized from DOPA, without any lipid compounds) and the lipomelanin of the present invention, without any incorporated ultra-violet light absorbing compound. As can be noted from FIG. 2, melanin has an increased ability to absorb UVR over a broader range of wavelengths than does the unoxidized DOPA of FIG. 1. The lipomelanin of the present invention provides a UVR absorbance profile and quantity similar to that of melanin.

Figure 3:
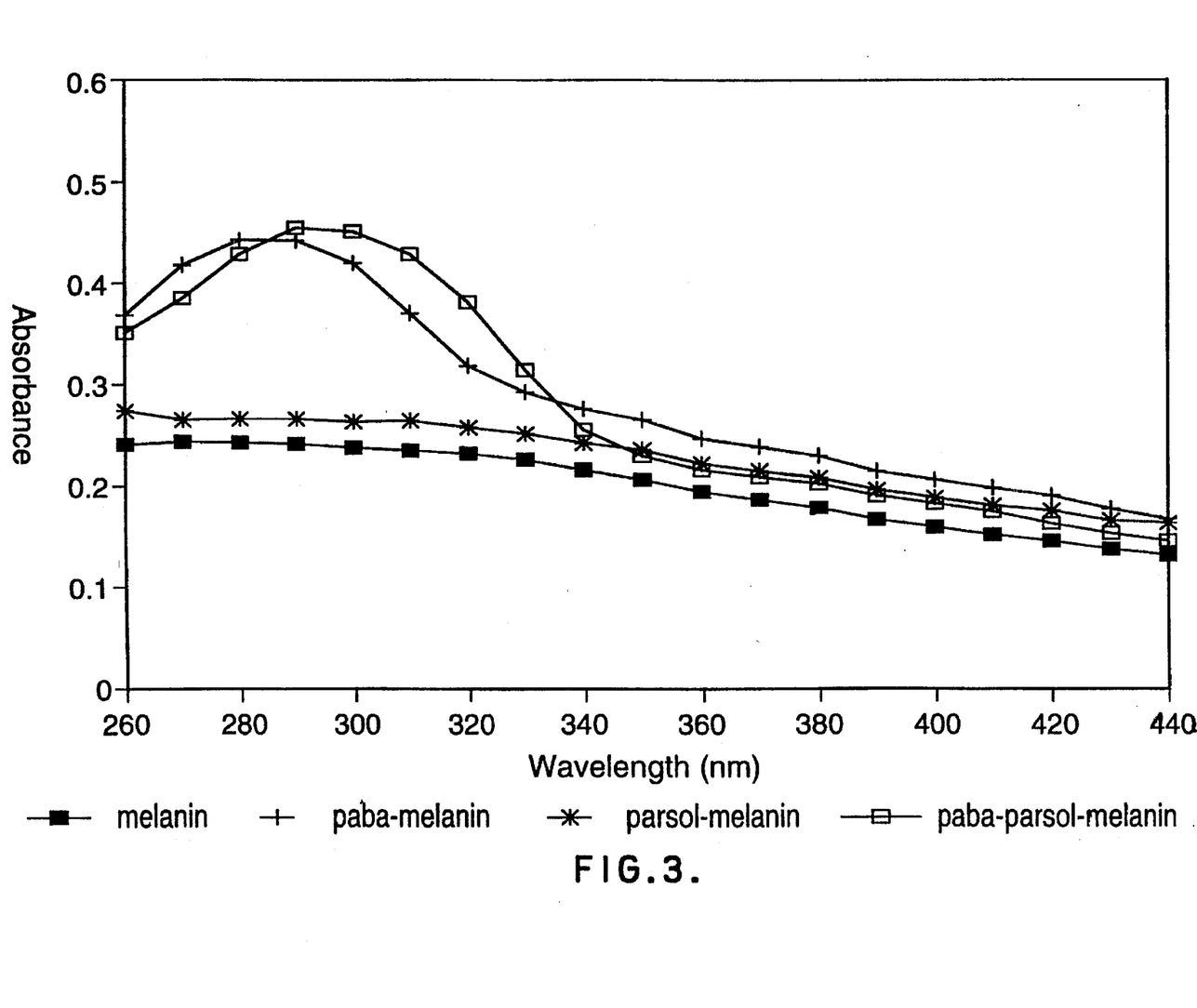
FIG. 3 shows the absorption spectra of melanin, paba-melanin, parsol-melanin and paba-parsol-melanin in the absence of an incorporated lipid.

FIG. 3 shows the absorption spectra of various melanins with ultra-violet light absorbing compounds. No lipid is included. The figure shows the spectra of: (a) melanin, (b) paba-melanin, (c) parsol-melanin and (d) paba-parsol melanin.

Figure 4:
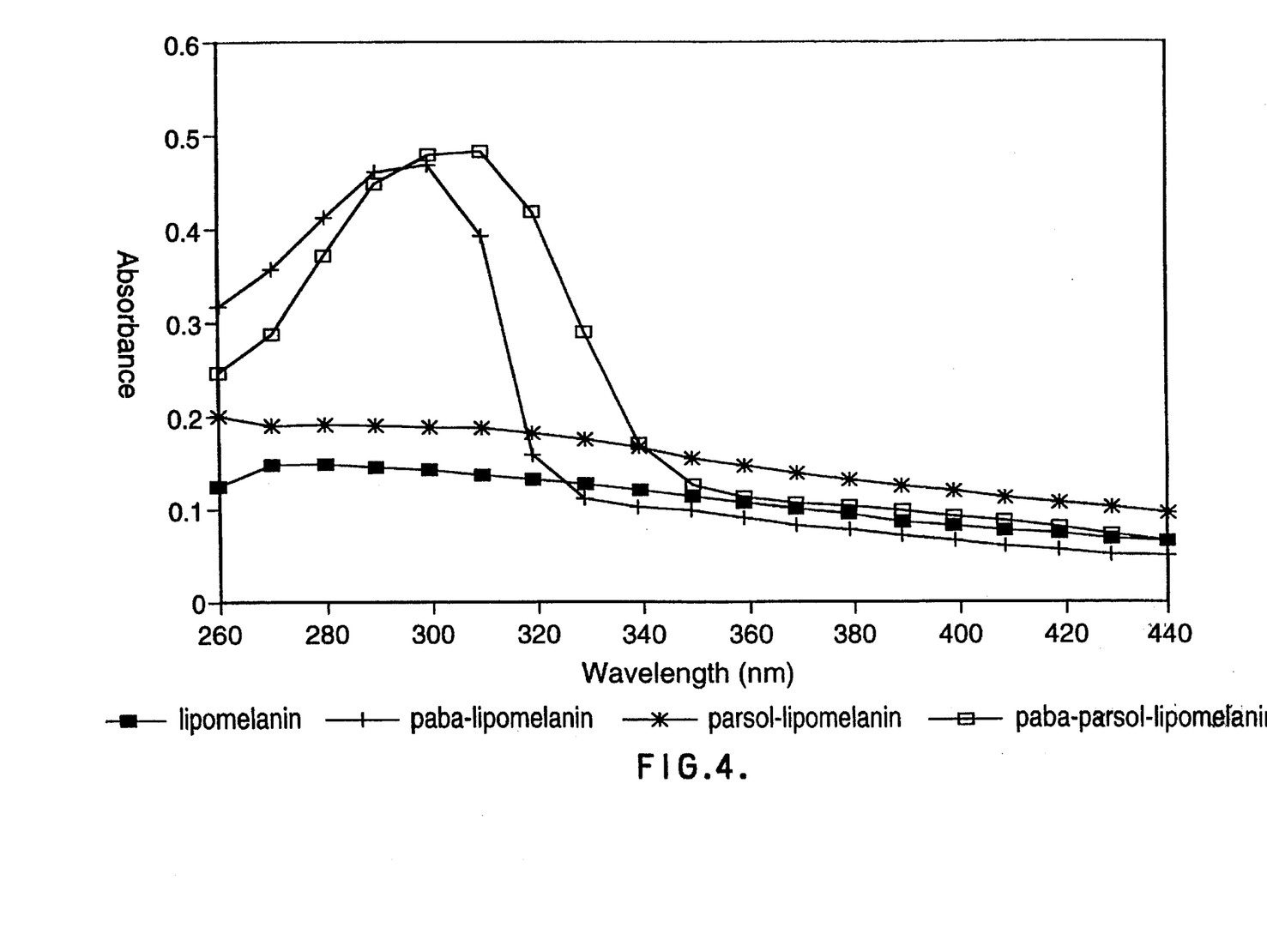
FIG. 4 shows the absorption spectra of lipomelanin, paba-lipomelanin, parsol-lipomelanin and paba-parsol-lipomelanin.

FIG. 4 is the absorption spectra of the lipomelanins of the present invention as follows: (a) lipomelanin without any ultra-violet light absorbing compounds, (b) paba-lipomelanin, (c) parsol-lipomelanin and (d) paba-parsol lipomelanin.

Figure 5:
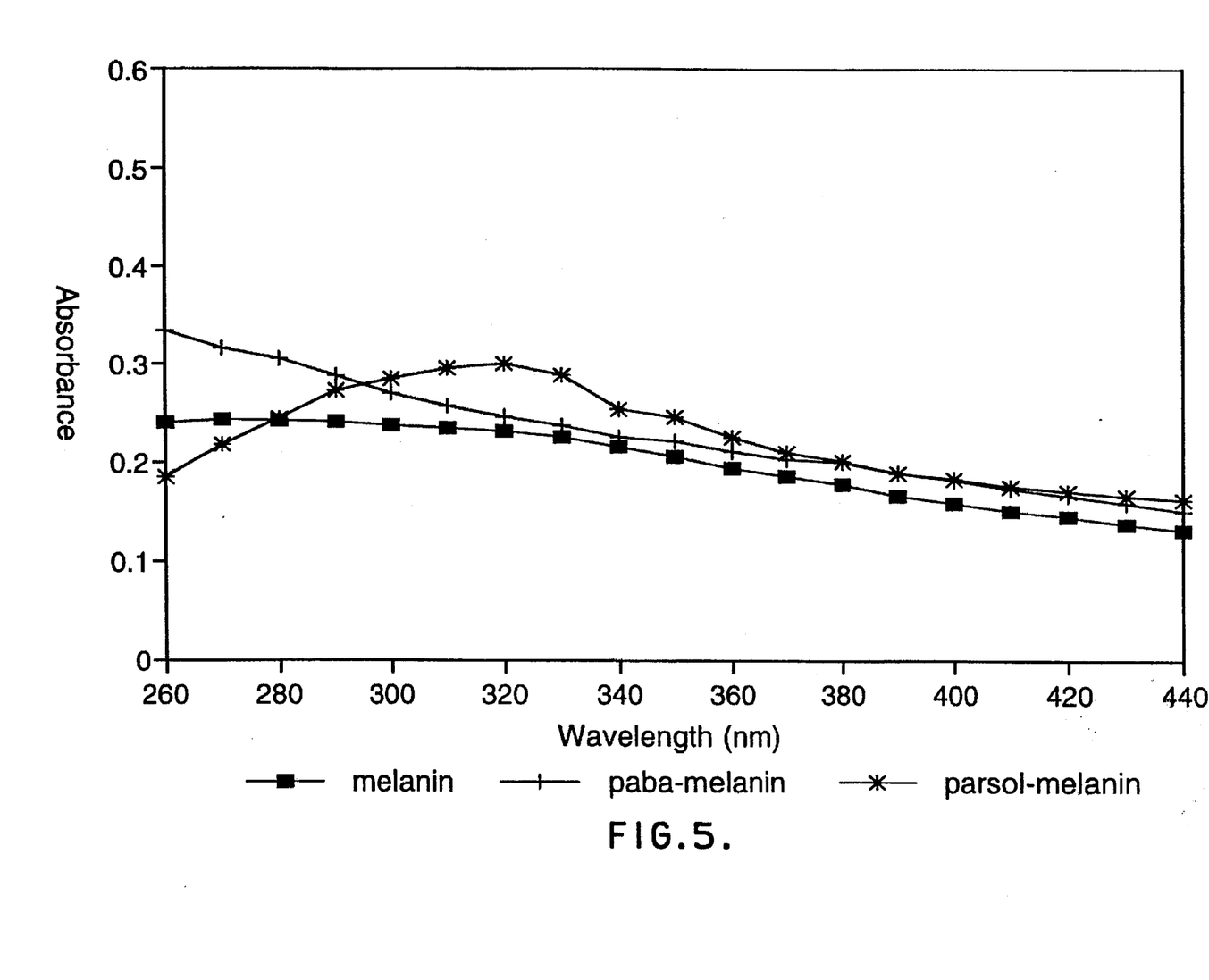
FIG. 5 shows the absorption spectra of melanin, paba-melanin and parsol-melanin, where the paba and parsol are added after the oxidation step.
Figure 6:
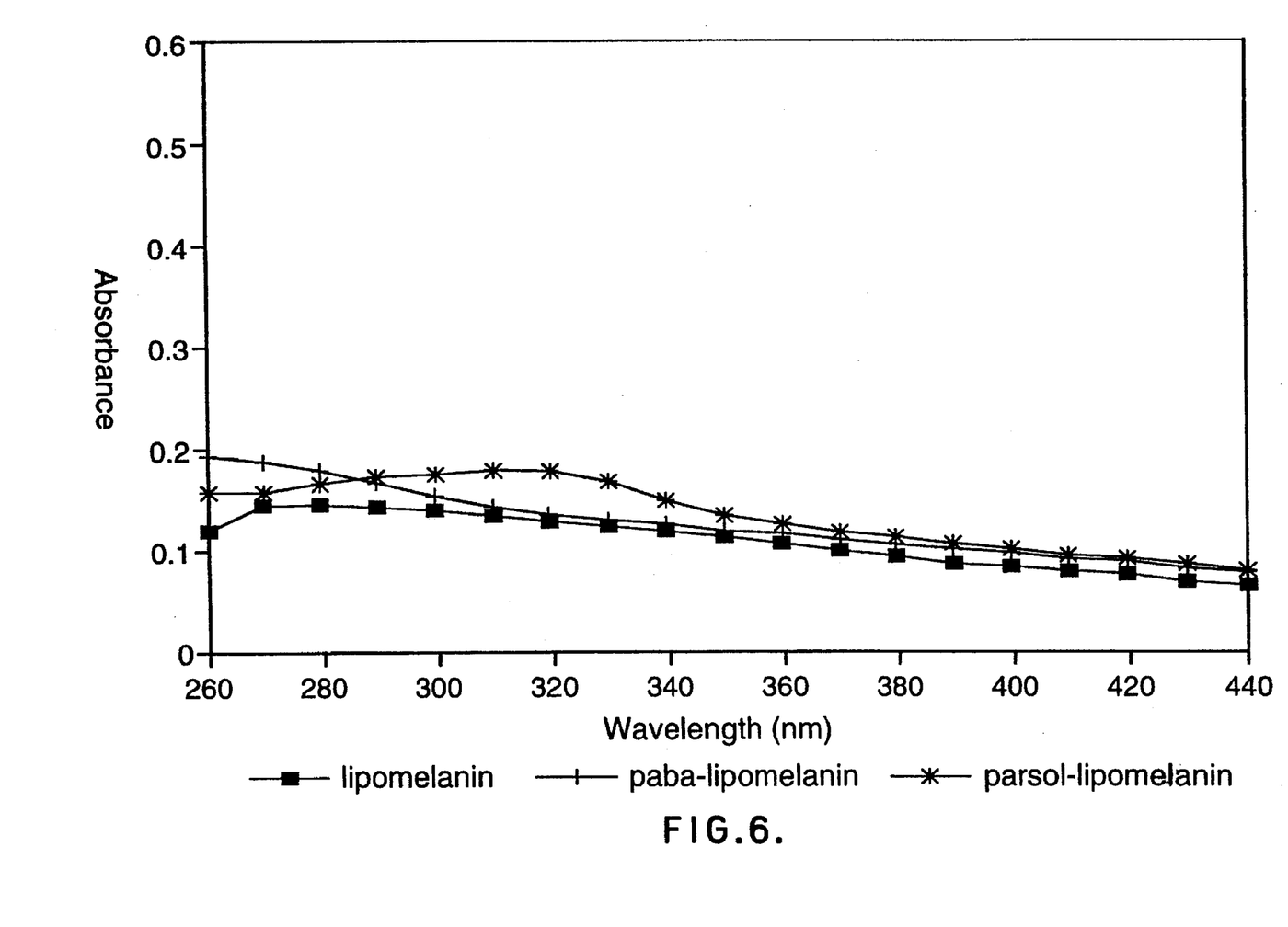
FIG. 6 shows the absorption spectra of lipomelanin, paba-lipomelanin and parsol-lipomelanin, where the paba and parsol are added after the oxidation step.

FIGS. 5 and 6 show the absorption spectra of various melanins and lipomelanins wherein the additional compounds (lipids and ultra-violet light absorbing compounds) are added to the melanin mixture after the oxidation. As can be seen from FIGS. 5 and 6, the addition of compounds after oxidation results in melanin and lipomelanin, ultra-violet light absorbing compound mixtures having lesser and flatter absorption spectra than the melanin lipomelanin mixtures of FIGS. 3 and 4 where the additional compounds are incorporated into the lipomelanin at the time of oxidation.

Figure 7:
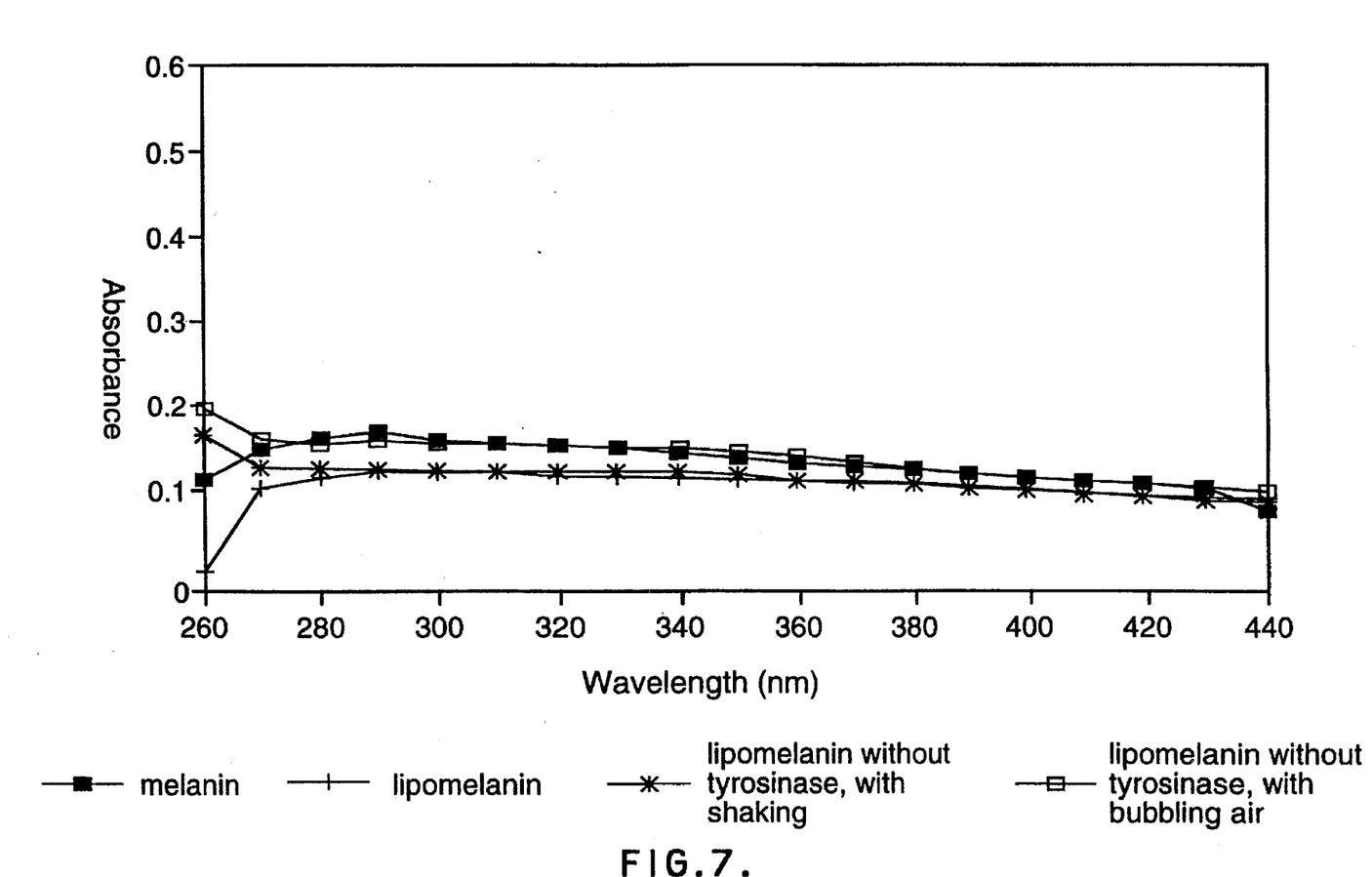
FIG. 7 shows the absorption spectra of lipomelanin (prepared with tyrosinase and by two preparation methods without tyrosinase)

FIG. 7 provides a comparison of lipomelanins prepared by the enzymatic oxidation of DOPA or oxidation of DOPA by aeration.

Figure 8:
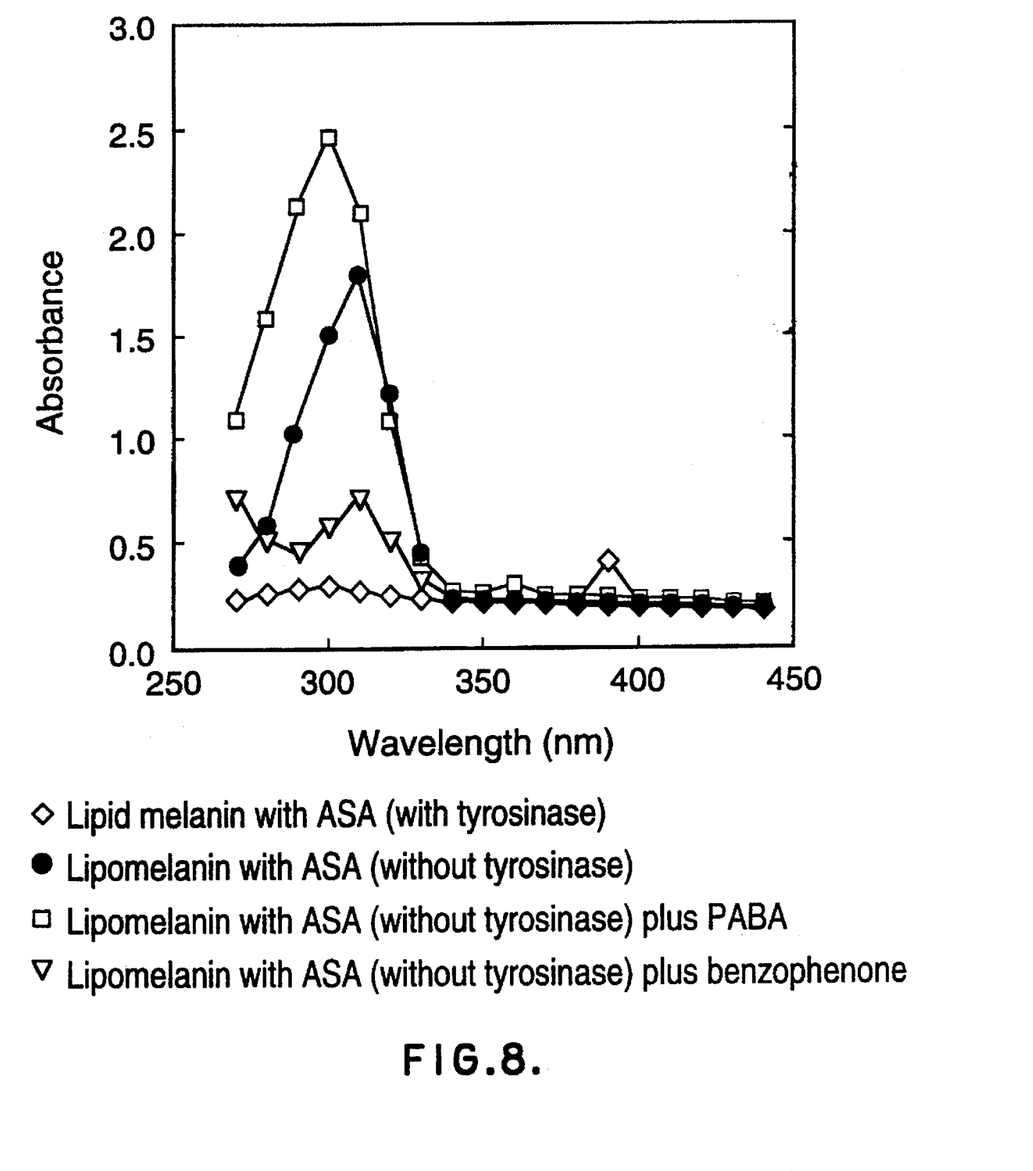
FIG. 8 shows the absorption spectra of lipomelanin with acetylsalicylic acid and either paba or benzophenone.

FIG. 8 shows the absorption spectra of melanins of the present invention prepared by various procedures. These include (a) lipomelanin with ASA prepared via enzymatic conversion of DOPA, (b) lipomelanin with ASA prepared via aeration without tyrosinase, (c) lipomelanin with ASA and paba prepared by aeration without tyrosinase, and (d) lipomelanin with ASA and benzophenone prepared via aeration with tyrosinase.

As can be seen from FIG. 8, the incorporation of into the lipomelanin polymer was increased using the aeration process of the present invention. Both paba and ASA were incorporated into the lipomelanin, although benzophenone is not incorporated in large amounts, and may also act to reduce ASA incorporation, due to its relative insolubility in water.

The textural characteristics of the lipomelanin sunscreen of the present invention make it suitable for application directly onto the skin. The lipid component of the lipomelanin promotes absorbtion of the composition by the skin. In addition, the lipomelanin of the present invention is creamy and smooth at physiological pH, and suitable for topical application.

A lipomelanin of the present invention may be combined with other ingredients to form a sunscreen composition. These ingredients may include substances typically found within creams, oils, ointments and lotions applied to the skin. Further, the added ingredients may function simply as diluents, or may optionally function to integrate additional utility into the composition. Coloring agents that may impart some additional ultra-violet-light protective value may also be added such as zinc oxide or titanium dioxide. Non-limiting examples of suitable ingredients for incorporation into such a composition include oils, such as mineral oil, jojoba oil and mink oil, emollients, vitamins, fragrances, dyes, colouring agents, pigments, water and any other ingredients typically added to skin-care compositions.

Aspects of the present invention will now be described by reference to the following specific non-limiting examples.

EXAMPLE 1

Enzymatic Preparation of Lipomelanin from DOPA

A solution containing 200 mg DOPA, 0.2 ml linoleic acid (0.642 mmoles, Sigma Chemical Company) and 20 mg purified mushroom tyrosinase (3,310–3,870 units/mg, Sigma Chemical Company) in 50 ml 0.05M phosphate buffer (pH 6.8) was incubated with shaking and exposure to air at 37° C. for 16 hours. The lipomelanin was acidified to pH 3 and 1.0M and sedimented by centrifugation at 1,000 g for 10 min. The supernatant was discarded and the melanin was dissolved in 10 ml 0.1M sodium hydroxide solution. The lipomelanin was precipitated by adding 1.0M hydrochloric acid to pH 3.0. The lipomelanin was then sedimented by centrifugation at 1,000 g for 10 minutes.

The lipomelanin was redissolved and resedimented by centrifugation following the same procedure three times more. The lipomelanin was then suspended in 5 ml water, and stored at 4° C. until further use.

EXAMPLE 2

Preparation of Lipomelanin by Autooxidation of DOPA

A solution containing 500 mg DOPA and 0.5 ml linoleic acid (Sigma Chemical Company) in 250 ml 0.1M phosphate buffer at pH 8.0 was prepared. Air was bubbled through the solution at room temperature (approximately 21° C.) for 16 hours. The lipomelanin was isolated by sedimenting, redissolving and resedimenting as described in Example 1.

Increased yields of lipomelanin can be achieved by autooxidation of DOPA using the following procedure. A solution containing 200 mg DOPA in 50 ml 0.1M phosphate buffer at pH 8.0 was aerated by bubbling air through the solution at room temperature for 3 hours. 0.2 ml linoleic acid was then added and aeration continued for a further sixteen hours. The lipomelanin was isolated by sedimenting, redissolving and resedimenting as described in Example 1.

EXAMPLE 3

Preparation of Lipomelanin with Additional Compounds

A solution containing 0.5 g DOPA in 250 ml 0.1M phosphate buffer at pH 8.0 was prepared. Air was bubbled through the solution at room temperature (approximately 21° C.) for 3 hours. 0.5 ml linoleic acid and 0.5 g paba were added. Aeration continued for an additional 12 hours. The lipomelanin/paba sunscreen was isolated by sedimentation, redissolving, and resedimenting as described in Example 1.

The lipomelanin/paba sunscreen prepared according to Example 3 is creamy and smooth for use in accordance with the sunscreen compositions of the present invention. It is more soluble in water at neutral pH than melanins alone, and soluble for use in accordance with the sunscreens of the present invention. Absorption properties of the lipomelanin/paba in the range of short wavelength UVB is high, as indicated in FIG. 4.

EXAMPLE 4

Preparation of Lipomelanin with Lecithin

A solution containing 200 mg DOPA, 0.642 mmoles lecithin and 20 mg purified mushroom tyrosinase (3,310–3,870 units/mg, Sigma Chemical Company) in 50 ml 0.05M phosphate buffer (pH 6.8) was incubated with shaking and exposure to air at 37° C. for 16 hours. The lipomelanin was acidified to pH 3.0 and 1.0M and sedimented by centrifugation at 1,000 g for 10 min. The supernatant was discarded and the lipomelanin was dissolved in 10 ml 0.1M sodium hydroxide solution. The lipomelanin was precipitated by adding 1.0M hydrochloric acid to pH 3.0. The lipomel was then sedimented by centrifugation at 1,000 g for 10 minutes.

The lipomelanin was redissolved and resedimented by centrifugation following the same procedure three times more. The lipomelanin was then suspended in 5 ml water, and stored at 4° C. until further use.

EXAMPLE 5

Preparation of Lipomelanins with Two Ultra-violet-light Absorbing Compounds.

A solution containing 200 mg (1.01 mmole) DOPA, in 50 ml $PO_4$ buffer at pH 8.0 was aerated by shaking for three hours at room temperature. 500 mg of paba (3.65 mmoles) in 45 ml of $PO_4$ buffer and 0.2 ml (0.642 mmoles) linoleic acid and 0.4 ml (2.38 mmoles) cinnamic acid ethyl ester were then added. Aeration continued for a further 16 hours. The lipomelanin/paba sunscreen complex was isolated as described in Example 1.

An alternate lipomelanin sunscreen incorporating paba and parsol was prepared as follows. A solution containing 200 mg (1.01 mmole) DOPA, in 50 ml $PO_4$ buffer at pH 8.0 was aerated by shaking for three hours at room temperature. 500 mg of paba (3.65 mmoles) in 45 ml of $PO_4$ buffer and 0.2 ml (0.642 mmoles) linoleic acid and 0.2 ml Parsol 1789 were then added. Aeration continued for a further 16 hours. The lipomelanin sun screw was isolated as described in Example 1. The absorption spectrum of the resulting compound (paba-parsol-lifomelanin) is shown in FIG. 4.

Other embodiments or variations are possible within the sphere and scope of the present invention. All such modifications and variations are believed to be within the sphere and scope of the present invention as defined by the claims appended hereto.

We claim:

1. A lipomelanin composition having a lipid moiety and a melanin moiety, the lipomelanin comprising a melanin substantially covalently bonded to an unsaturated lipid, and wherein said unsaturated lipid is a fat, phosphoglyceride, or fatty acid.

2. The lipomelanin of claim 1, wherein the unsaturated lipid is selected from the group comprising unsaturated: fatty acids, triglycerides, diglycerides, monoglycerides, esters of fatty acids, lecithins, cephalins, phosphatidyl ethanolamine, phosphatidyl dimethylethanolamine, phosphatidyl monomethylethanolamine, phosphastidyl inositol, phosphatidyl serine and phosphatidic acid.

3. The lipomelanin of claim 2, wherein the unsaturated fatty acid is selected from the group consisting of arachidonic acid, oleic acid, linoleic acid, and linolenic acid.

4. The lipomelanin of claim 1, wherein the lipid comprises linoleic acid.

5. The lipomelanin of claim 1, wherein the melanin is selected from the group comprising eumelanins and pheomelanins.

6. The lipomelanin of claim 1, wherein the ratio of the lipid moiety to the melanin moiety ranges from about 0.6:1 to about 1:1.

7. A method for creating a lipomelanin composition comprising the steps:

dissolving in water a compound selected from the group of melanin precursors consisting of DOPA and DOPA analogs, whereby an aqueous solution is formed having a concentration of about 10 to about 20 millimoles per liter;

adding an unsaturated lipid which is a fat, phosphoglyceride or fatty acid to the aqueous solution, to form a concentration of about 6 to about 12 millimoles per liter thus forming a reaction mixture;

reacting the reaction mixture in the presence of oxygen for a sufficient period of time to form a lipomelanin-containing solution; and isolating the lipomelanin from the lipomelanin-containing solution.

8. The method of claim 7 wherein the DOPA analogs are selected from the group consisting of naturally occurring DOPA analogs and synthetic DOPA analogs.

9. The method of claim 7 wherein the DOPA analogs are selected from the group consisting of hydroquinone, cathechol, o-quinone, p-quinone, DOPA methyl ester, dihydroxyphenylacetic acid, dihydroxyphenyl glycol and dihydroxyphenyl serine.

10. The method of claim 7, wherein the lipid is selected from the group consisting of unsaturated: triglycerides, diglycerides, monoglycerides, esters of fatty acids, lecithins, cephalins, phosphatidyl ethanolamine, phosphatidyl dimethylethanolamine, phosphatidyl monomethylethanolamine, phosphastidyl inositol, phosphatidyl serine and phosphatidic acid.

11. The method of claim 7, wherein the unsaturated lipid is a fatty acid selected from the group comprising arachidonic acid, oleic acid, linoleic acid and linolenic acid.

12. The method of claim 11, wherein the fatty acid is linoleic acid.

13. The method of claim 7 wherein reacting the reaction mixture comprises the steps:

adding an enzyme to the reaction mixture; and agitating the reaction mixture in the presence of oxygen.

14. The method of claim 13 wherein the enzyme comprises tyrosinase.

15. The method of claim 14 wherein the concentration of said tyrosinase in the reaction mixture is about 20 to about 21 millimoles/liter, and the activity of said tyrosinase is about 3,310 to about 3,870 units per milligram.

16. The method of claim 15 wherein the pH of the reaction mixture is maintained at about 6.7 by using a phosphate buffer in a concentration of about 0.05 moles per liter, and the temperature of the reaction mixture is maintained at about 37 degrees centigrade for a period of about 16 hours.

17. The method of claim 7 wherein reacting the reaction mixture comprises the steps:

controlling the pH in the range of about 6 to about 10; and agitating the reaction mixture in the presence of oxygen.

18. The method of claim 17 wherein the pH is controlled within a range of about 8 to about 10.

19. The method of claim 17 wherein the pH is controlled using a buffer.

20. The method of claim 19 wherein the buffer is a phosphate buffer at a pH of about 8.

21. The method of claim 7 wherein the oxygen is provided by bubbling air through the reaction mixture.

22. The method of claim 7 wherein the reaction continues for at least about 12 to about 16 hours.

23. A method for producing a lipomelanin compound formed by the autooxidization of a melanin precursor in the presence of an unsaturated lipid to form a lipomelanin, comprising the steps:

dissolving in water a compound selected from the group of melanin precursors, whereby an aqueous solution having a concentration of about 10 to about 20 millimoles melanin precursor per liter is formed;

adding an unsaturated lipid which is a fat, phosphoglyceride or fatty acid to the aqueous solution to form a concentration of about 6 to about 7 millimoles lipid per liter, thus forming a reaction mixture;

reacting the reaction mixture in the presence of oxygen for at least about 12 to about 16 hours to form a lipomelanin.

24. The method of claim 23 wherein the melanin precursor is one or more compounds selected from the group consisting of DOPA and DOPA analogs.

25. The method of claim 23 wherein the melanin precursor is 3,4-dihydroxyphenylalanine.

26. The method of claim 23 wherein the pH of the reaction mixture is controlled at about pH 7 to about pH 10.

* * * * *

UNITED STATES PATENT AND TRADEMARK OFFICE
CERTIFICATE OF CORRECTION

PATENT NO. : 5,643,554
DATED : 07/01/97
INVENTOR(S) : I. ARAVINDAKSHAN MENON et al.

It is certified that error appears in the above-identified patent and that said Letters Patent is hereby corrected as shown below:

<u>IN THE TITLE</u>  Item [54]       and Column 1, Line 1)
   Delete "LIPOMELANIM" and insert - - LIPOMELANIN - - .

At column 5, line 46-47, after the words "chemically bonded to a lipid" please delete "compound".

<u>IN THE DETAILED DESCRIPTION OF THE INVENTION</u>

At column 8, line 24, after the words "sulisobenzone, dioxybenzone, menthyl anthranilate and" please add - - Parsol 1789. - -.

At column 9, line 59, after the phrase "As can be seen from Fig. 8, the incorporation of", please add - - ASA - - .

At column 11, line 27, please delete "lipomel" and add - - lipomelanin - - .

At column 11, line 45, please delete "complex".

UNITED STATES PATENT AND TRADEMARK OFFICE
CERTIFICATE OF CORRECTION

PATENT NO. : 5,643,554
DATED : 07/01/97
INVENTOR(S) : I. ARAVINDAKSHAN MENON et al.

It is certified that error appears in the above-identified patent and that said Letters Patent is hereby corrected as shown below:

At column 11, line 54, please delete "sun screw" and add - - sunscreen - - .

At column 11, line 56 please delete "lifomelanin" and add - - lipomelanin - - .

Signed and Sealed this

Third Day of February, 1998

BRUCE LEHMAN

Attest:

Attesting Officer

Commissioner of Patents and Trademarks